United States Patent
Barth et al.

(10) Patent No.: US 10,182,776 B2
(45) Date of Patent: Jan. 22, 2019

(54) SYSTEM AND METHOD FOR CORRELATING OBJECT INFORMATION WITH X-RAY IMAGES

(71) Applicant: SIEMENS HEALTHCARE GMBH, Erlangen (DE)

(72) Inventors: Karl Barth, Hoechstadt (DE); Adrian Egli, Geuensee (CH); Rainer Graumann, Hoechstadt (DE); Adrian John, Kaisten (CH); Gerhard Kleinszig, Forchheim (DE); Wei Wei, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 229 days.

(21) Appl. No.: 15/024,463

(22) PCT Filed: Jul. 15, 2014

(86) PCT No.: PCT/EP2014/065137
§ 371 (c)(1),
(2) Date: Mar. 24, 2016

(87) PCT Pub. No.: WO2015/043793
PCT Pub. Date: Apr. 2, 2015

(65) Prior Publication Data
US 2016/0228078 A1 Aug. 11, 2016

(30) Foreign Application Priority Data
Sep. 24, 2013 (DE) .................. 10 2013 219 134

(51) Int. Cl.
*A61B 6/00* (2006.01)
*A61B 6/12* (2006.01)
(Continued)

(52) U.S. Cl.
CPC .......... *A61B 6/4417* (2013.01); *A61B 5/0077* (2013.01); *A61B 6/00* (2013.01);
(Continued)

(58) Field of Classification Search
None
See application file for complete search history.

(56) References Cited

U.S. PATENT DOCUMENTS

| 5,539,798 A | 7/1996 | Asahina et al. |
| 6,227,704 B1 | 5/2001 | Bani-Hashemi et al. |

(Continued)

FOREIGN PATENT DOCUMENTS

| DE | 10049103 B4 | 7/2001 |
| DE | 102006004692 A1 | 8/2007 |

(Continued)

*Primary Examiner* — Hoon Song
(74) *Attorney, Agent, or Firm* — Laurence Greenberg; Werner Stemer; Ralph Locher

(57) ABSTRACT

A system for displaying an image includes at least one x-ray source for emitting radiation, a detector for acquiring the radiation emitted by the radiation source for generating an x-ray image, the detector being disposed opposite the radiation source in relation to an object to be examined, a computer unit for performing computational operations, a display device for displaying x-ray images acquired by the detector and at least one data acquisition unit for acquiring surface information of the object to be examined. The data acquisition unit is disposed on the detector side and the computer unit is configured to correlate the data acquired by the detector-side data acquisition unit with the x-ray image.

11 Claims, 3 Drawing Sheets

(51) Int. Cl.
  *G01N 23/04* (2018.01)
  *A61B 5/00* (2006.01)
  *A61B 6/08* (2006.01)
  *A61B 6/04* (2006.01)
(52) U.S. Cl.
  CPC .......... *A61B 6/08* (2013.01); *A61B 6/12* (2013.01); *A61B 6/461* (2013.01); *A61B 6/463* (2013.01); *A61B 6/5205* (2013.01); *A61B 6/5247* (2013.01); *G01N 23/04* (2013.01); *A61B 6/0492* (2013.01); *G01N 2223/323* (2013.01)

(56) References Cited

U.S. PATENT DOCUMENTS

| | | | |
|---|---|---|---|
| 6,435,717 B1* | 8/2002 | Kohler | A61B 6/107 378/205 |
| 7,465,090 B2 | 12/2008 | Haras | |
| 8,213,574 B2 | 7/2012 | Banckwitz et al. | |
| 8,731,268 B2 | 5/2014 | Li et al. | |
| 8,837,673 B2 | 9/2014 | Graumann | |
| 2009/0285357 A1 | 11/2009 | Khamene et al. | |
| 2011/0222656 A1* | 9/2011 | Matoba | G01N 23/083 378/62 |
| 2012/0170824 A1 | 7/2012 | Hendriks et al. | |
| 2014/0161222 A1* | 6/2014 | Tsuyuki | G01N 23/046 378/19 |

FOREIGN PATENT DOCUMENTS

| | | |
|---|---|---|
| DE | 102006025357 A1 | 12/2007 |
| DE | 102007023029 A1 | 11/2008 |
| DE | 102009033675 A1 | 2/2011 |
| DE | 112010001224 T5 | 4/2012 |
| DE | 102011005659 A1 | 9/2012 |
| EP | 1084678 A1 | 3/2001 |

\* cited by examiner

SYSTEM AND METHOD FOR CORRELATING OBJECT INFORMATION WITH X-RAY IMAGES

BACKGROUND OF THE INVENTION

Field of the Invention

The invention relates to a system and a method for correlating object information obtained on the detector side with X-ray images, and in particular the use of said object information.

DE 100 49 103 B4 discloses a system for superimposing X-ray and video images. To that end, a mirror/camera system is mounted on the side of the X-ray emitter. This has the consequence that during the use of this system, contrary to current practice, the X-ray source of the C-arm has to be positioned above the patient. This arrangement of the X-ray source results in increased exposure of the user to stray radiation arising from the radiation source. Another problem results from the fact that the user relatively often has to look away from the therapy site and view the monitor in order to be able to see the displayed optical image superimposed with an X-ray image.

BRIEF SUMMARY OF THE INVENTION

It is an object of the present invention to prevent the user from being exposed to increased stray radiation, but at the same time also to provide the possibility of generating additional information for the user.

The object is achieved by a system and a method described below. Further features configuring the invention are also described below.

The way in which the object is achieved is described below with regard to the claimed method. Features, advantages or alternative embodiments mentioned here are likewise also applicable to the other subjects claimed, and vice versa. In other words, the substantive claims (which are directed for example to a system, a device or to a product) can also be developed by the features described or claimed in association with the method. In this case, the corresponding functional features of the method are implemented by corresponding substantive modules, in particular by hardware or microprocessor modules. Moreover, the sequence of the method steps can be varied, if appropriate.

A system according to the invention for displaying an image comprises at least one X-ray source for emitting radiation, a detector for acquiring the radiation emitted by the X-ray source for generating an X-ray image, wherein the detector is arranged opposite the X-ray source in relation to an object to be examined, a computer unit for carrying out computational operations, a display device for displaying X-ray images acquired by the detector, and at least one data acquisition unit for acquiring surface information of the object to be examined, wherein the data acquisition unit is arranged on the detector side and the computer unit is designed to correlate the data acquired by the detector-side data acquisition unit with the X-ray image. The detector-side arrangement of the data acquisition unit, that is to say the arrangement on the side of the detector instead of the arrangement on the side of the X-ray source, makes it possible to avoid the increased stray radiation for the user. At the same time, however, the surface information acquired by the data acquisition unit, such as brightness and/or color information and/or depth information and/or contour information, can nevertheless be provided for further use. Correlation of this information is necessary, however, since the surface information is recorded from the opposite direction with respect to the X-ray source. As a result, the position data of the information obtained are inversed with respect to the X-ray image, that is to say that the central ray of a viewing pyramid starting from the center of the detector runs opposite to the central ray of the projection pyramid proceeding from the X-ray source. Generally the terms viewing cone and projection cone are also employed, but they actually apply only to circular acquisition fields or detectors. In this case, the object to be examined may be a patient, but also an article.

The data acquisition unit can comprise at least one camera. One camera suffices to obtain brightness and color information of the surface, for example. In particular, two or more cameras can also be present, such that a stereo technique becomes possible, as is used for example in Kinect technology. Information about the surface contour and shape can also be obtained as a result. Furthermore, the data acquisition unit preferably comprises at least one light beam device, such as e.g. a laser device. In particular, said laser device is suitable for carrying out a laser distance measurement. In an alternative embodiment, it can be used alternatively or cumulatively as a laser projector for a light-section method for measuring surfaces. In this respect, a combination of the laser device with one or a plurality of cameras is also extremely advantageous.

The system can also comprise a projection device for projecting points, lines, contours and/or areas onto the object to be examined. As projector, a laser projector is suitable, but other video projectors can also be used. LED projectors or DLP projectors can be mentioned as possible examples. This makes it possible to project the surface information obtained onto the object to be examined. As a result, the user can obtain relevant information, without having to look away from the object to be examined.

The system preferably furthermore comprises an input unit for processing the X-ray image displayed on the display device in order to determine the points, lines, contours and/or areas to be projected using the projection device. In this case, the input unit can be embodied as a touchscreen, but can also have other customary input aids, such as a mouse, a keyboard or the like. In this regard, information such as courses of bones or vessels from the X-ray image can be applied to the object. The points, lines, contours and/or areas to be projected can thus also be created manually or semi-automatically, rather than being determined exclusively by the computer unit by means of automatic algorithms, by the user being given the opportunity to input confirmation signals for the automatically created points, lines and contours, etc., on a provided user interface of a computer unit.

It is particularly preferred if the data acquisition unit is arranged with at least one part, but in particular with all components, outside the radiation region of the radiation source. As a result, the X-ray image obtained is no longer adversely affected by the data acquisition unit.

As already mentioned, the acquired surface information can be color information, position information and/or depth information. In this case, the position information relates to the x- and y-coordinates in a plane parallel to the detector plate, and the depth information z in a direction perpendicular to the x-y plane. As a result the contours and outlines of the surface can then also be reconstructed and e.g. superimposed with an X-ray image, or else be projected onto the object.

A method according to the invention for correlating acquired surface data of an object to be examined with an X-ray image comprises at least the steps of generating an X-ray image of an object to be examined, of acquiring surface information of the object to be examined by means of a detector-side data acquisition unit, and of correlating the acquired surface data with the generated X-ray image. In principle, however, it is also possible to replace the step of generating an X-ray image by reading in X-ray images already present (which can be read in e.g. from a memory or a database). It should then be taken into consideration, however, that the X-ray image read in can also be related to the information obtained by the data acquisition unit, e.g. by means of specific markers which can be represented and identified equally as reference points by X-ray device and data acquisition unit and which are related to one another by so-called registration.

In particular, the method also comprises the step of superimposing the correlated surface data with the generated X-ray image or projecting them onto the examined object. The surface data can be color information, position information and/or depth information.

The method can furthermore comprise the steps of recording the surface by means of at least one first camera for acquiring the surface information, of determining the distance between a point on the surface of the object and the camera, and of determining the projection of the point in the X-ray image. This is a simple possibility for assigning the image information to the corresponding points on the X-ray image. The steps of recording the surface of the object by means of two cameras arranged at a distance from one another, and of calculating the surface information from the data obtained by the camera can furthermore also be comprised. The steps of traversing the surface of the object with a light line, recording the light line by means of a camera, and calculating the surface information from the data obtained by the camera are likewise possible.

The method preferably comprises the steps of creating points, lines, contours and/or areas at an input unit, projecting the created points, lines, contours and/or areas onto the object to be examined. In this case, creating can be carried out automatically, semi-automatically or else manually.

The above-described embodiments of the method according to the invention can also be implemented as a computer program product comprising a computer program, wherein the computer is caused to carry out the above-described method according to the invention if the computer program is executed on the computer or on a processor of the computer. In this case, the computer can be provided as an individual workstation or be linked into a computer network (e.g. LAN, WLAN, WAN network, cloud etc.).

BRIEF DESCRIPTION OF THE SEVERAL VIEWS OF THE DRAWING

The following description of the figures discusses exemplary embodiments, which should not be understood to be restrictive, with their features and further advantages with reference to the drawing, in which.

DESCRIPTION OF THE INVENTION

Figure 1:
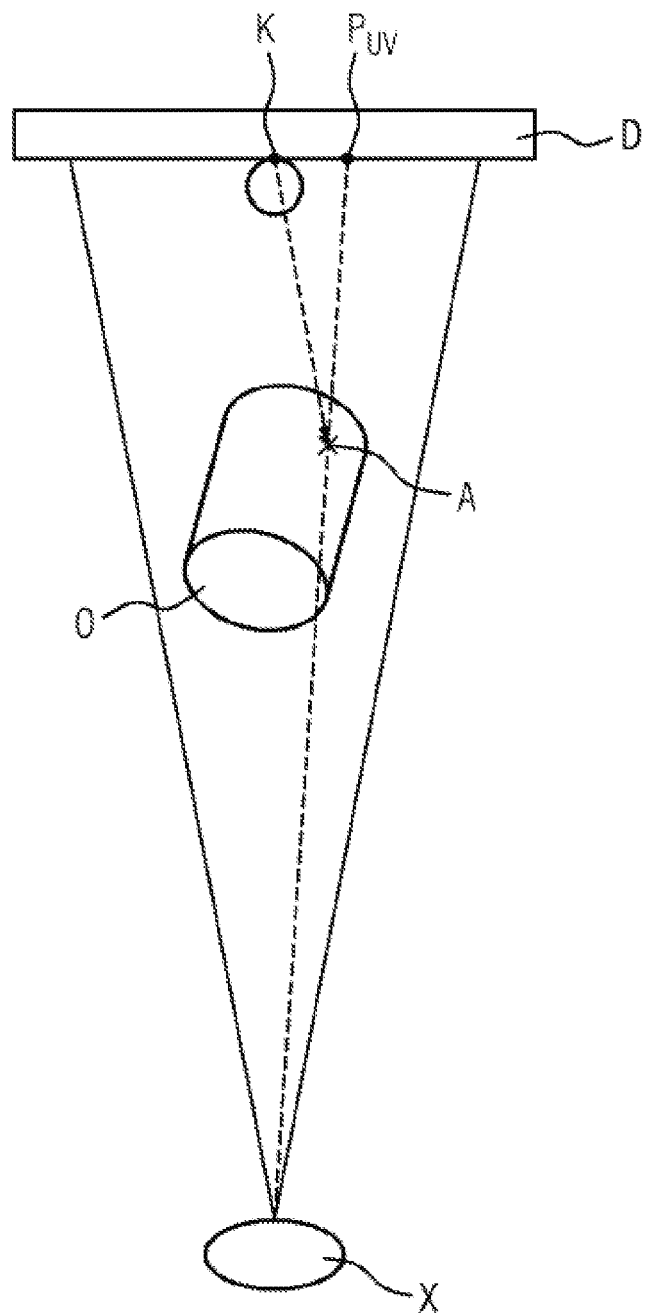
FIG. 1 shows a schematic illustration of a system for correlating acquired surface data and a generated X-ray image.

FIG. 1 shows a system for correlating acquired surface data and a generated X-ray image. In this case, additional information about an object O to be examined is obtained and coordinated with the X-ray image, such that the information can be superimposed with the X-ray image. FIG. 1 reveals an X-ray source X, an object O, a detector D and a data acquisition unit K, which is embodied here as a camera K. The system also comprises a display, on which the X-ray image and, if appropriate, also superimposed surface information can be seen.

The camera K preferably contains a unit for distance measurement, such as, for example, a laser for measuring the distance to the object surface or a motion camera that can likewise be used to measure distances. In principle, however, it is possible for the distance measuring unit also to be positioned elsewhere. However, it is important here that the relative position with respect to the camera and/or with respect to the X-ray source is known. In the present case, the camera is arranged centrally opposite the X-ray source. This allows a relatively simple assignment of the camera to the X-ray source and an optimum overview of the examined object O. However, this position of the camera K is not optimal with regard to a created X-ray image, since the camera can constitute a disturbance factor for the X-ray image. In principle, therefore, the camera K can also be positioned laterally at the detector. One variant is for e.g. a 45° inclined mirror transparent to X-rays to be fitted centrally in front of the detector, such that the central ray of the camera firstly runs parallel to the detector before it is directed by the mirror onto the central ray of the X-ray projection.

Surface information, such as information about brightness and color of the object O, for example is obtained by means of the camera K. The distance between the individual points of the surface of the object O and the camera K can be obtained by means of the distance measurement. A computer unit can automatically also calculate (from these data sets) the depth information of the point A, that is to say its position perpendicular to the detector plane. The x- and y-coordinates of the point can be obtained via the recording geometry of the camera. In this regard, the surface of the object O can be scanned point by point and the information about the contour of the surface can be obtained. In this case, each point is related to the X-ray image (image registration methods can be used here). In this regard, for the various points of the X-ray image which is detected by the detector, the additional information of the corresponding surface points of the examined object can be obtained and in particular also correlated, superimposed, embedded and/or imaged with the X-ray image.

In order to establish the association of the individual surface points of the object O and the respective coordinates of the X-ray image, for example a point on the object can be marked as a reference point, and from this marked point, which can also be seen in the X-ray image, the respective coordinates of the other surface points can be related. However, this requires the examined object O to be provided with a marker or to contain an anatomical landmark which is visible both to the data acquisition unit K and to the X-ray source, such that the reference point is present in both recordings. The computer unit can then calculate therefrom the association between the X-ray image and acquired surface information.

Another possibility consists in measuring the distance to the respective surface points and then establishing the relation of the surface points to the pixels of the X-ray image by means of the known relative positions of camera, distance measuring unit and X-ray source. By way of example, this is clarified on the basis of the point A situated on the surface of the object O in FIG. 1. By means of the distance measurement situation for example at the center of the camera K, a 3D pixel is found in the camera coordinates. Since the relative position of the camera K with respect to the X-ray source X is known, the X-ray that passes through the point A can be calculated by means of the likewise known projection geometry of the X-ray device. This found X-ray projects the point A into the point $P_{uv}$ on the detector plane, such that its image coordinates u and v in the X-ray image are known. As a result, that point in the detector plane which corresponds to the point A on the surface is obtained and the additional surface information can be provided at this point of the X-ray image. This method is very similar to a triangulation method.

In this regard, for example, the X-ray image can be enriched by (real) brightness and/or color information of the object to be examined in the region of a lesion, but position information of the point A can also be stored, such that the surface contour of the object can be displayed from a multiplicity of surface points. The transfer of the color value $A_{rgb}$ to the point $P_{UV}$ in the detector plane can then be carried out by means of a glare factor that is between 0 and 1. Here the superimposition of camera and X-ray image is then equal to $\alpha \times P_{UV} + (1-\alpha) \times A$ (color value).

The system can be extended by two or more cameras and/or two or more laser systems being fitted on the detector side, for example oppositely on the left and right at the detector. In an embodiment having exclusively cameras, a stereo technique is used to obtain a 3D relief of the imaging and then to convert said relief into the projection geometry of the X-ray system. Identical partial structures on the object surface are identified for this purpose.

It is likewise also possible to use a laser system that can obtain the 3D surface information, for example by the projection of moving line patterns that can be recorded and measured by at least one camera (light section). With the use of a plurality of cameras, the quality of the measurement of the line pattern projections increases here. Other usable methods for obtaining surface information, depending on the use of light projectors and the number of cameras, include phase shift methods or the coded light approach, for example. It is thus possible to generate, from an observer position opposite the X-ray source, images that geometrically correspond to the X-ray projections, such that the generated three-dimensional information of the contour of the surface can be directly superimposed with the X-ray images. In this regard, a 2D X-ray image on which the surface contour of the object O is superimposed then arises.

With these methods, specific instruments and tools can also be displayed in their correct position in the X-ray image. The stereo segmentation can also be simplified in this respect by virtue of the fact that the instruments, for example, "actively" image themselves by virtue of the fact that applied markers, LEDs or fluorescent ink, for example, are/is identified by the cameras, the position on the X-ray image is calculated and the contour of the instrument is superimposed with the X-ray image. In particular, it is advantageously possible to have recourse to databases in which the data of the instruments (e.g. the outline) are stored.

Figure 2:
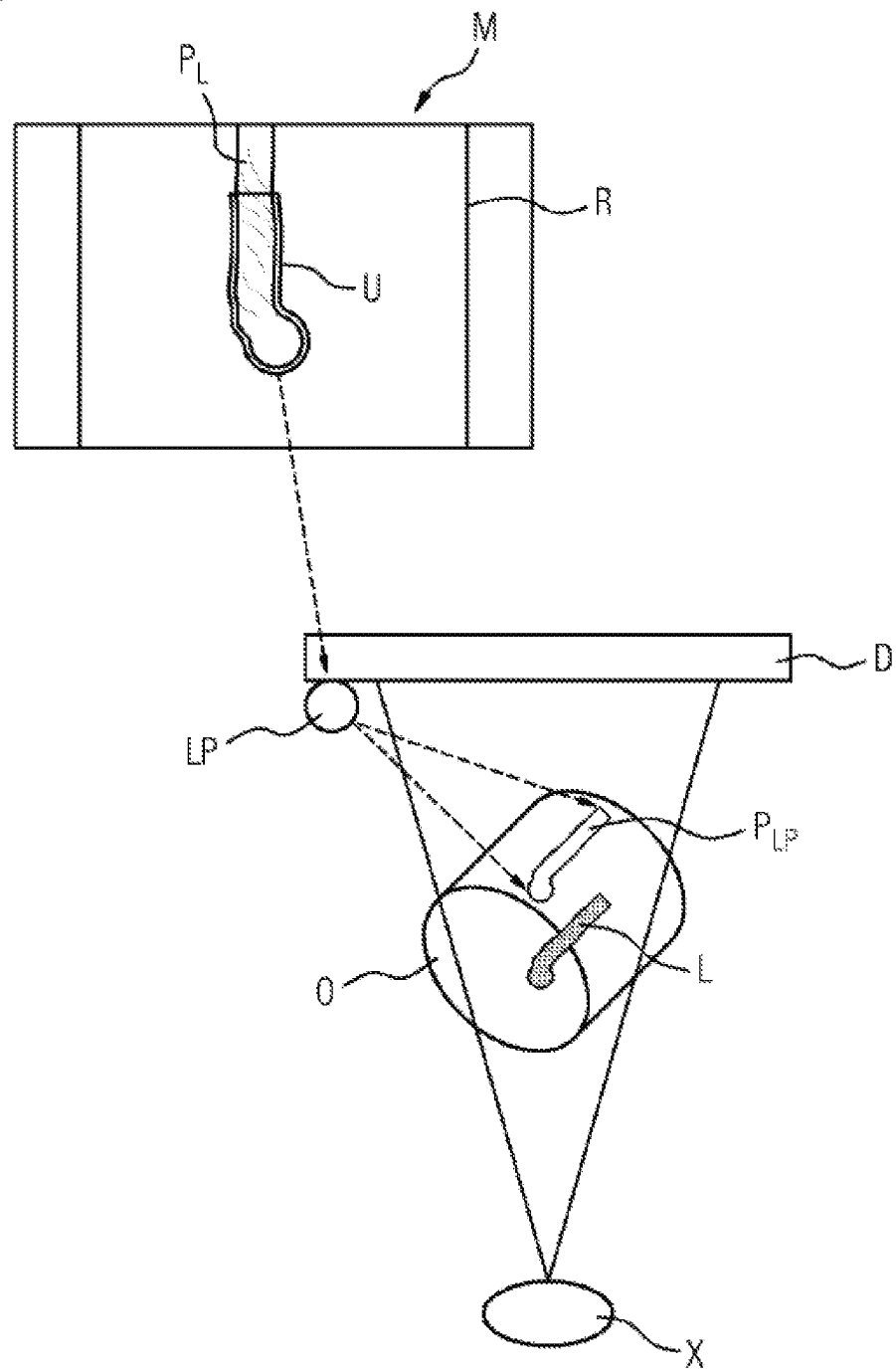
FIG. 2 shows a system for projecting outlines onto an examination object.

The system can preferably comprise a laser projector LP, which is likewise fitted on the detector side. This can be seen in FIG. 2. Furthermore, the system comprises a display, on which the X-ray images R created or read in can be seen. The monitor of the display can be embodied as a touchscreen, such that a pattern can be generated on the display manually or by means of an aid, such as a pen (stylus) for a touchscreen. However the pattern can also be generated on the display by conventional operating elements such as a mouse or a keyboard. The pattern can thus be created manually by means of the aids/operating elements mentioned. However, this can also be created automatically by a computer with corresponding software, or semi-automatically in a combination. In this case, the pattern is arbitrary and can comprise points, lines, contours and/or areas, for example. In particular, contours originating from lesions or outlines which can be seen on the X-ray image are intended to be displayed thereby. In this regard, a lesion L in the object O can be discerned in FIG. 2, for example, said lesion being imaged onto the detector D as contour $P_L$ by means of an X-ray recording. The image is then displayed on the display M and the imaging of the lesion $P_L$ is depicted as a contour manually on the monitor. Alternatively, for example, the contour can also be created semi-automatically by virtue of the associated contour being identified automatically by tapping of the imaging $P_L$. As a further option, the contour can also be created fully automatically by predefined limit values of gray-scale values. This outline U can then project the contour onto the object O by means of the projection device LP. In order to ensure a correct representation of the projection $P_{LP}$ on the surface of the object, it should be taken into consideration that the surface being "drawn" on is an irregular surface which must be measured beforehand in 3D by the methods mentioned above, e.g. once again by means of a laser and including taking account of the respective X-ray geometry. One very useful variant of the method consists in the user marking an anatomical region in the X-ray image R (e.g. punctiform, encompassing geometrical figure, manually defined contour, overall image, also multiple markings) and then all the markings being displayed according to the X-ray projection geometry on the visible surface on the patient.

As a result of the projection $P_{LP}$ of the X-ray information onto the surface of the patient (object), the physician can continue to look at the patient for a much longer time. As a result of the X-ray superimposition, e.g. on the skin, the physician obtains position-correct information from the depth—e.g. bone contours or courses of vessels. With suitable light intensity or setting of the color (color temperature), the image can be visualized very well. One preferred embodiment is realized by a segmentation being carried out in the X-ray image (e.g. bones or vessels) and the structures thus identified then being drawn on the treatment environment (e.g. skin surface) as "vector graphics" by a laser.

Figure 3:
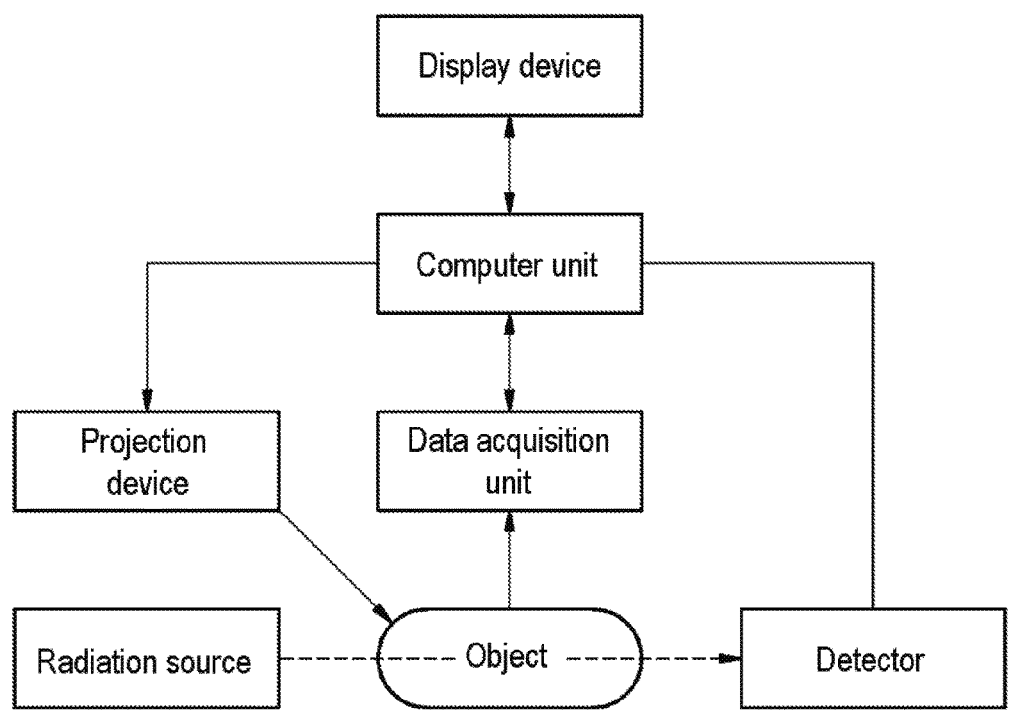
FIG. 3 shows a block diagram of an exemplary system of the present invention.

FIG. 3 shows a block diagram of a device which is suitable for carrying out all the methods mentioned above. The device comprises a display device with an input device, a data acquisition limit, a computer unit, a projection device, a detector and a radiation source. The radiation source irradiates the object, the detector detects the radiation and the resulting image can be displayed on the display device. The data acquisition unit acquires the surface information, the computer unit correlates said information with the X-ray image, and the correlated results can be superimposed with the X-ray image and/or projected onto the object (or else in other directions).

Finally, it should be pointed out that the description of the invention and the exemplary embodiments, in principle, should not be understood to be restrictive with regard to a specific physical realization of the invention. This is obvious to a person skilled in the art, in particular, that the invention can be realized partly or completely in software and/or hardware and/or in a manner distributed among a plurality of physical products—in this case in particular also computer program products.

The invention claimed is:

1. A system for displaying an image, the system comprising:
   at least one X-ray source for emitting radiation;
   a detector for acquiring the radiation emitted by said at least one X-ray source for generating an X-ray image, said detector being disposed opposite said at least one X-ray source relative to an object to be examined;
   a display device for displaying X-ray images acquired by said detector;
   at least one detector-side data acquisition unit for acquiring surface information of an exterior surface of the object to be examined, said at least one detector-side data acquisition unit including at least one camera with a distance measuring unit;
   a computer unit for carrying out computational operations, said computer unit being configured to correlate data acquired by said at least one detector-side data acquisition unit with the X-ray image; and
   a projection device connected to said computer unit and configured to project a visible image related to the X-ray image onto the exterior surface of the object to be examined.

2. The system according to claim 1, wherein said at least one detector-side data acquisition unit includes at least one laser device.

3. The system according to claim 1, which further comprises a projection device for projecting at least one visible marker selected from the group consisting of points, lines, contours and areas onto the object to be examined.

4. The system according to claim 3, which further comprises an input unit for processing the X-ray image displayed on said display device in order to determine the at least one of points, lines, contours or areas to be projected.

5. The system according to claim 1, wherein said at least one detector-side data acquisition unit is disposed outside a radiation region of said at least one X-ray source.

6. The system according to claim 1, wherein said at least one detector-side data acquisition unit is configured to acquire at least one of brightness information, color information, position information or depth information.

7. A method for correlating acquired surface data of an object to be examined with an X-ray image, the method comprising the following steps:
   generating an X-ray image of the object to be examined;
   acquiring surface information of the object to be examined using a detector-side data acquisition unit by recording a surface using at least one first camera for acquiring the surface information;
   determining a distance between a point on the surface of the object and the camera;
   determining a projection of the point in the X-ray image; and
   correlating acquired surface data with the generated X-ray image, superimposing the correlated surface data with the generated X-ray image, and projecting a visible image related to the correlated surface data onto the object.

8. The method according to claim 7, wherein the surface data are color information or depth information.

9. The method according to claim 7, which further comprises the following steps:
   recording the surface of the object by using the at least one first camera in the form of two cameras disposed at a distance from one another; and
   calculating the surface information from data obtained by the cameras.

10. The method according to claim 7, which further comprises the following steps:
    traversing the surface of the object with a light line;
    recording the light line by using the at least one first camera; and
    calculating the surface information from data obtained by the at least one first camera.

11. The method according to claim 7, which further comprises the following steps:
    creating at least one of points, lines, contours or areas at an input unit; and
    projecting the created at least one of points, lines, contours or areas onto the object to be examined.

* * * * *